(12) United States Patent
Tolborg et al.

(10) Patent No.: US 11,427,843 B2
(45) Date of Patent: Aug. 30, 2022

(54) **PROCESS FOR PRODUCING AN AZAPHILONE IN *TALAROMYCES ATROROSEUS***

(71) Applicant: DANMARKS TEKNISKE UNIVERSITET, Kgs. Lyngby (DK)

(72) Inventors: Gerit Tolborg, Dyssegård (DK); Thomas Isbrandt Petersen, Virum (DK); Thomas Ostenfeld Larsen, Holte (DK); Mhairi Workman, Kgs. Lyngby (DK)

(73) Assignee: DANMARKS TEKNISKE UNIVERSITET, Kgs. Lyngby (DK)

( * ) Notice: Subject to any disclaimer, the term of this patent is extended or adjusted under 35 U.S.C. 154(b) by 297 days.

(21) Appl. No.: 16/611,066

(22) PCT Filed: May 8, 2018

(86) PCT No.: PCT/EP2018/061898
§ 371 (c)(1),
(2) Date: Nov. 5, 2019

(87) PCT Pub. No.: WO2018/206590
PCT Pub. Date: Nov. 15, 2018

(65) Prior Publication Data
US 2020/0165645 A1 May 28, 2020

(30) Foreign Application Priority Data

May 8, 2017 (EP) .................................... 17169959

(51) Int. Cl.
| | | |
|---|---|---|
| *C12P 17/18* | (2006.01) | |
| *A23L 5/46* | (2016.01) | |
| *A61K 8/49* | (2006.01) | |
| *C07D 491/048* | (2006.01) | |
| *C12N 1/14* | (2006.01) | |

(52) U.S. Cl.
CPC ............... *C12P 17/188* (2013.01); *A23L 5/46* (2016.08); *A61K 8/49* (2013.01); *C07D 491/048* (2013.01); *C12N 1/14* (2013.01); *A23V 2002/00* (2013.01)

(58) Field of Classification Search
None
See application file for complete search history.

(56) References Cited

U.S. PATENT DOCUMENTS

2011/0250656 A1 * 10/2011 Mapari .................. C09B 61/00
106/31.77

FOREIGN PATENT DOCUMENTS

WO WO 2012/022765 A1 * 2/2012 ............. C09B 61/00

OTHER PUBLICATIONS

International Search Report and Written Opinion dated Aug. 1, 2018, Intl. Application No. PCT/EP2018/061898, 19 pages.
Kim et al.; "Antimicrobial activities of amino acid derivatives of monascus pigments." FEMS Microbiol Lett 2006, 264:117-124.
Rasmussen et al.; "Talaromyces atroroseus—Genome sequencing, Monascus pigments and azaphilone gene cluster evolution." Technical University of Denmark, Sep. 2015, 262 pages.

* cited by examiner

*Primary Examiner* — Brian J Davis
(74) *Attorney, Agent, or Firm* — Casimir Jones S.C.; Lisa Mueller

(57) ABSTRACT

The invention provides a novel class of natural azaphilone pigments, called atrorosins, and methods for their production. The methods for the production of atrorosins include production by fermentation using a fungal species belonging to the genus *Talaromyces*, preferably the species *Talaromycesatroroseus*. The use of the novel atrorosins pigments as a colouring agent for food items and/or non-food items, and for cosmetics.

14 Claims, 11 Drawing Sheets

Figure 2:
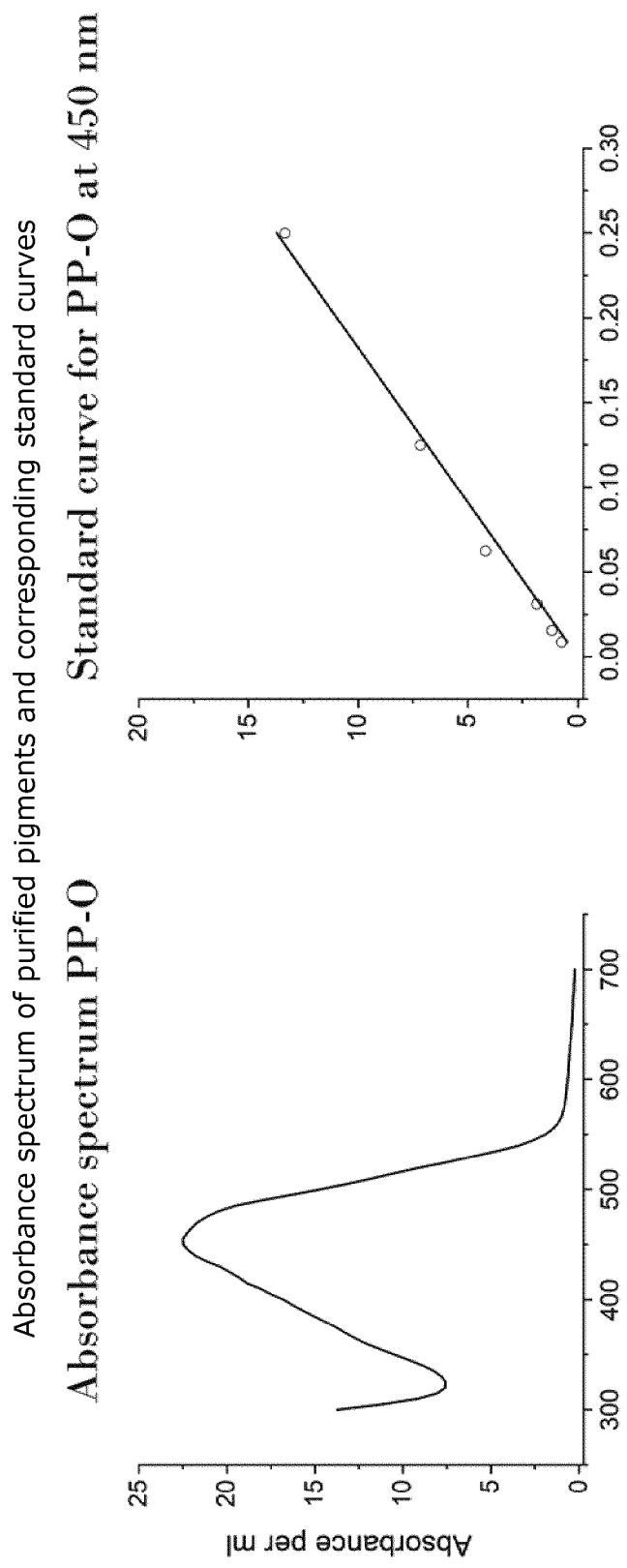

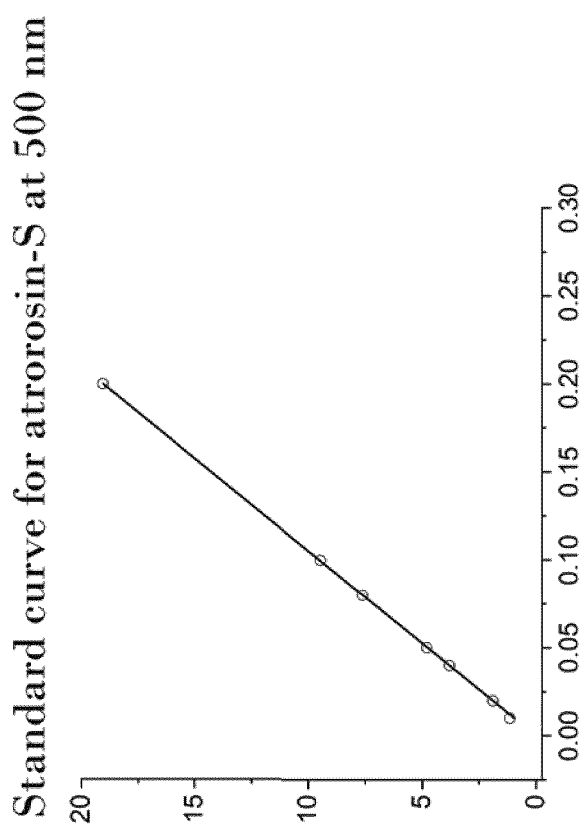
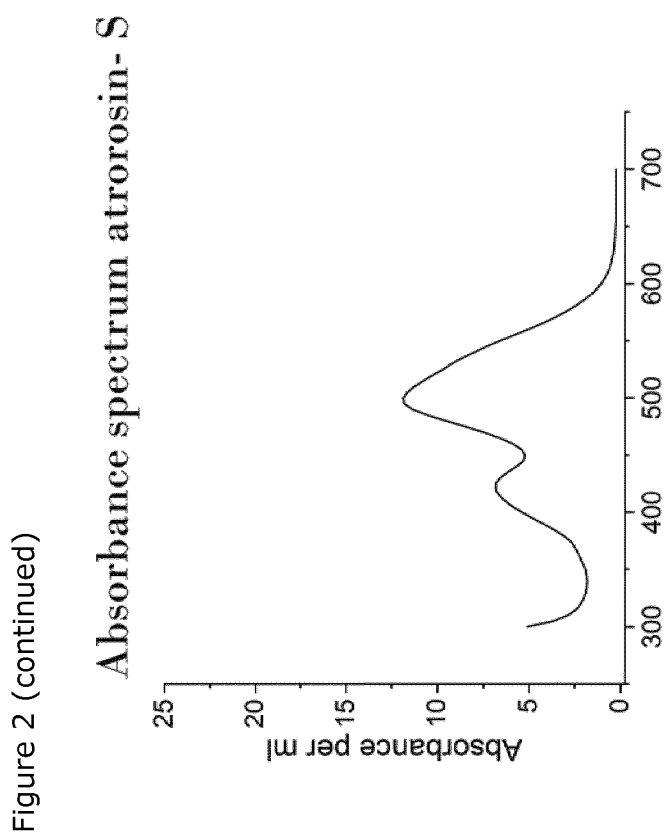
Figure 2 (continued)

| Amino Acid used as nitrogen source | uv chromatogram at 520 ± 10 nm | [M/Z] | pigment name |
|---|---|---|---|
| KNO3 | | m/z 412.1755<br>m/z 514.2072<br>m/z 541.2181<br>m/z 500.1915<br>m/z 542.2021 | PP-V<br>atrorosin-T<br>atrorosin-Q<br>atrorosin-S<br>atrorosin-E |
| Asp | | m/z 528.1864 | atrorosin-D |
| Glu | | m/z 542.2021 | atrorosin-E |
| His | | m/z 550.2184 | atrorosin-H |
| Ser | | m/z 500.1915 | atrorosin-S |

Figure 8 - A
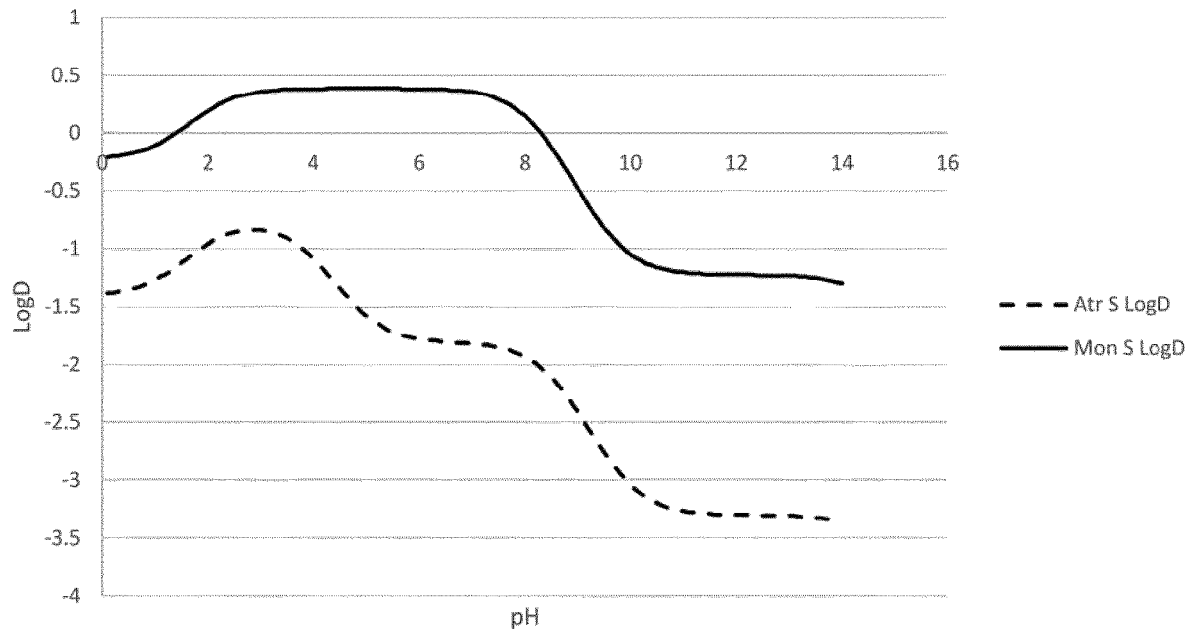
Figure 8 - B
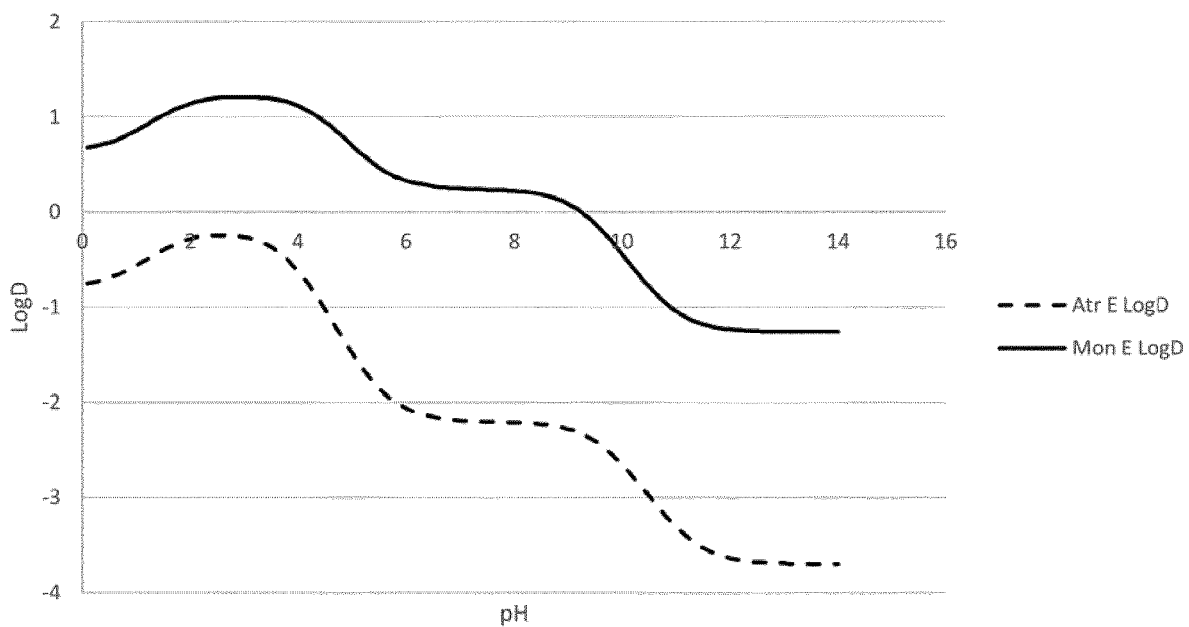

Figure 10 - A
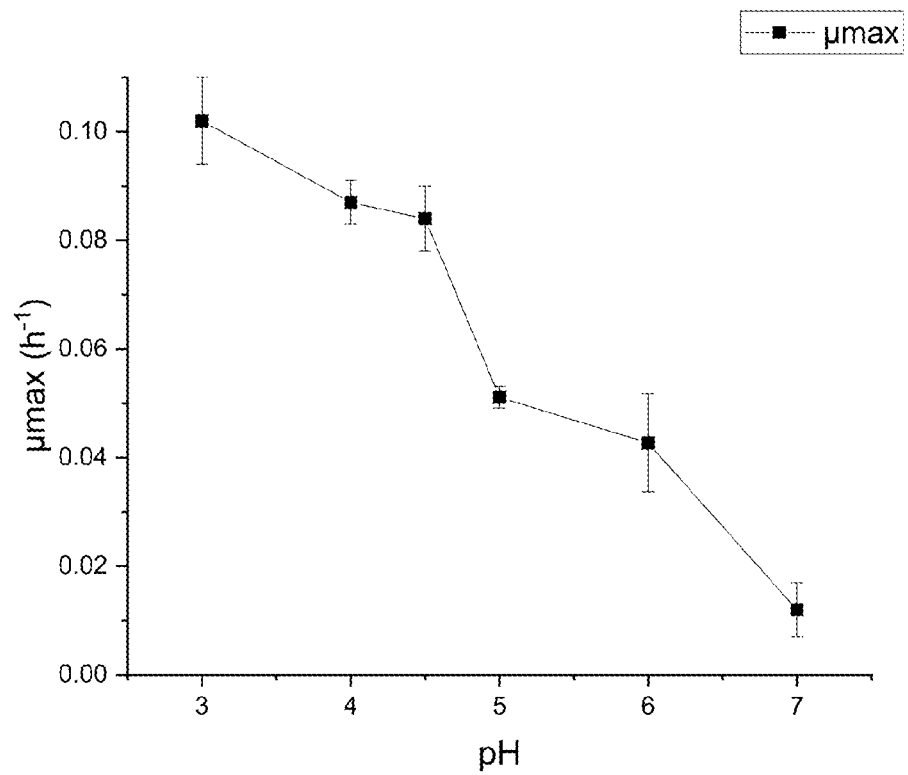
Figure 10 - B
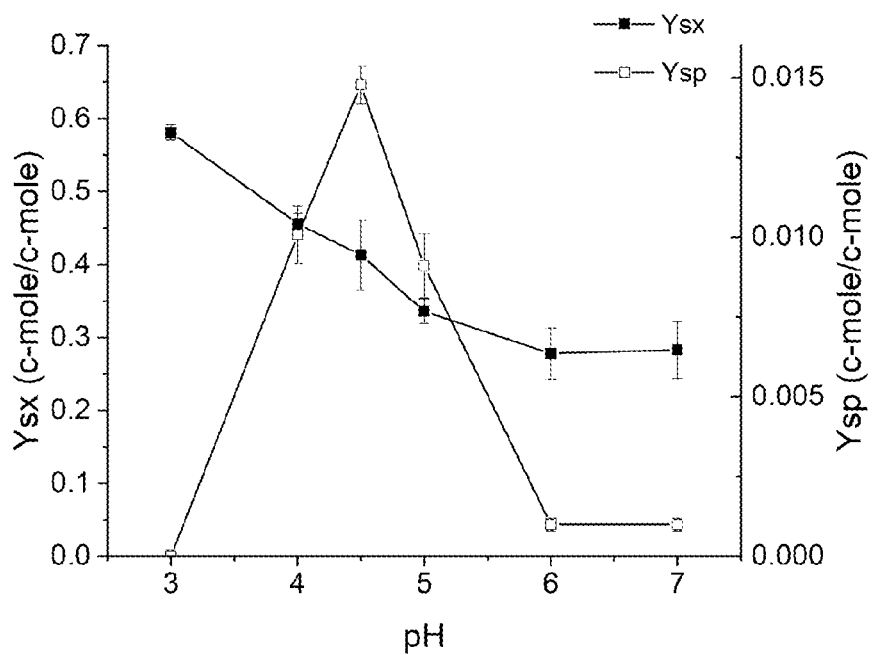

PROCESS FOR PRODUCING AN AZAPHILONE IN *TALAROMYCES ATROROSEUS*

FIELD OF THE INVENTION

The invention provides a novel class of natural azaphilone pigments, called atrorosins, and methods for their production. The methods for the production of atrorosins include production by fermentation using a fungal species belonging to the genus *Talaromyces*, preferably the species *Talaromyces atroroseus*. The use of the novel atrorosin pigments, and a kit comprising the same, as a colouring agent for food items and/or non-food items, and for cosmetics.

BACKGROUND OF THE INVENTION

Natural food colorants are increasingly sought after due to growing consumer awareness of potential harmful effects of synthetic colorants[1,2]. In view of the increasing recognition of a link between diet and health, the food additive industry faces new challenges in providing natural color alternatives. So far most industrially used natural colorants are extracted directly from natural sources e.g. anthocyanins (beet root *Beta vulgaris* extract), lycopene (tomato *Solanum lycopersicum* extract) or carminic acid (extracted from the female insect *Dactylopius coccus*[3]). Their production is highly dependent on the supply of raw ingredients, which are subject to seasonal variation both in regards to quantity and quality[4]. These limitations can be overcome by exploring new sources for natural pigments such as microorganisms[5]. Fungi are known to naturally biosynthesize and excrete diverse classes of secondary metabolites including pigments within a broad range of colors[6].

*Monascus* is a pigment-producing fungal genus that has long been used for the manufacture of traditional foods in Asian countries[7]. Pigments from *Monascus* are referred to as "*Monascus* pigments", which are a mixture of azaphilones including yellow, orange, and red constituents.

The use of species of *Monascus* for the production of *Monascus* pigments results in a cocktail of different *Monascus* pigments[8], having a range of hues, whose composition is difficult to control and can vary from batch-to-batch. In addition, species of *Monascus* are known to produce mycotoxins, such as citrinin[9], which causes diverse toxic effects, including nephrotoxic, hepatotoxic and cytotoxic effects and which excludes their use for industrial purposes in western countries. From an industrial perspective it would be highly preferable to produce these component pigments individually by fermentation, where the individual species of pigment produced was free of mycotoxins, such that the pigment can easily be extracted and recovered without the need for multiple and possibly complex purification steps. Among the important uses of natural pigments are as food additives; where water soluble pigments are highly desirable.

SUMMARY OF THE INVENTION

According to a first embodiment, the invention provides a method for producing an atrorosin pigment (preferably a single species of atrorosin pigment) by fermentation, comprising the steps of:

a) providing spores or mycelia of a species of the genus *Talaromyces*, b) cultivating the spores or mycelia of (a) in a liquid growth medium, c) recovering the atrorosin pigment produced during said cultivating step b), and d) optionally isolating said atrorosin pigment, wherein the pH of the growth medium in step (b) is maintained between 4 and 6; wherein the sole nitrogen source in said liquid growth medium in step (b) is one single compound selected from the group consisting of an amino acid, a peptide, an amino sugar and a primary amine; and wherein the atrorosin pigment has the structure of Formula I:

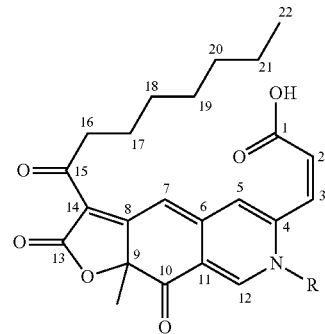

wherein N—R is selected from the group consisting of an amino acid, a peptide, an amino sugar and a primary amine, and the configuration of the double bond between carbon 2 and 3 is cis.

The method according to the first embodiment may further comprise the additional step of:

a') cultivating the spores or mycelia of (a) in a preliminary liquid growth medium, wherein the sole nitrogen source is an inorganic nitrogen source and the concentration of $NO_3^-$ is no more than 20 mM, continuing cultivation till the concentration of $NO_3^-$ is depleted to less than 5 mM;, and wherein said step (a') is followed by step (b).

According to a second embodiment the invention provides an atrorosin pigment having the structure of Formula I:

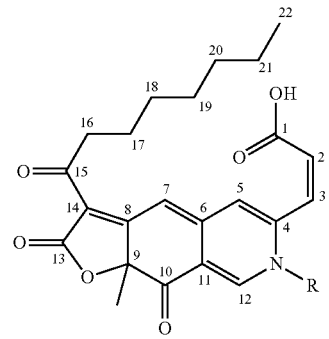

wherein N—R is selected from among an amino acid, a peptide, an amino sugar and a primary amine, and the configuration of the double bond between carbon 2 and 3 is cis, wherein said amino acid is selected from one of the group consisting of: L-alanine, L-arginine, L-asparagine, L-aspartate, L-cysteine, L-glutamate, L-glycine, L-histidine, L-isoleucine, L-leucine, L-lysine, L-methionine, L-phenylalanine, L-serine, L-threonine, L-tyrosine, L-valine and L-ornithine.

According to a third embodiment, the invention provides an atrorosin pigment having the structure of Formula I as defined above that is produced by the method of the invention.

According to a fourth embodiment, the invention provides for the use of the atrorosin pigment, having the structure of Formula I as defined above, as a colouring agent for any one of a food, a non-food product and a cosmetic.

According to a fifth embodiment, the invention provides a product comprising the atrorosin pigment having the structure of Formula I as defined above, wherein the product is selected from among a food, a non-food product and a cosmetic.

According to a sixth embodiment the invention provides a kit for coloring a product, wherein the kit comprises at least one atrorosin pigment having the structure of Formula I as defined above, wherein the pigment is supplied in a container, and wherein the product is selected from among a food, a non-food product and a cosmetic.

DESCRIPTION OF THE INVENTION

FIGURES

Figure 1:
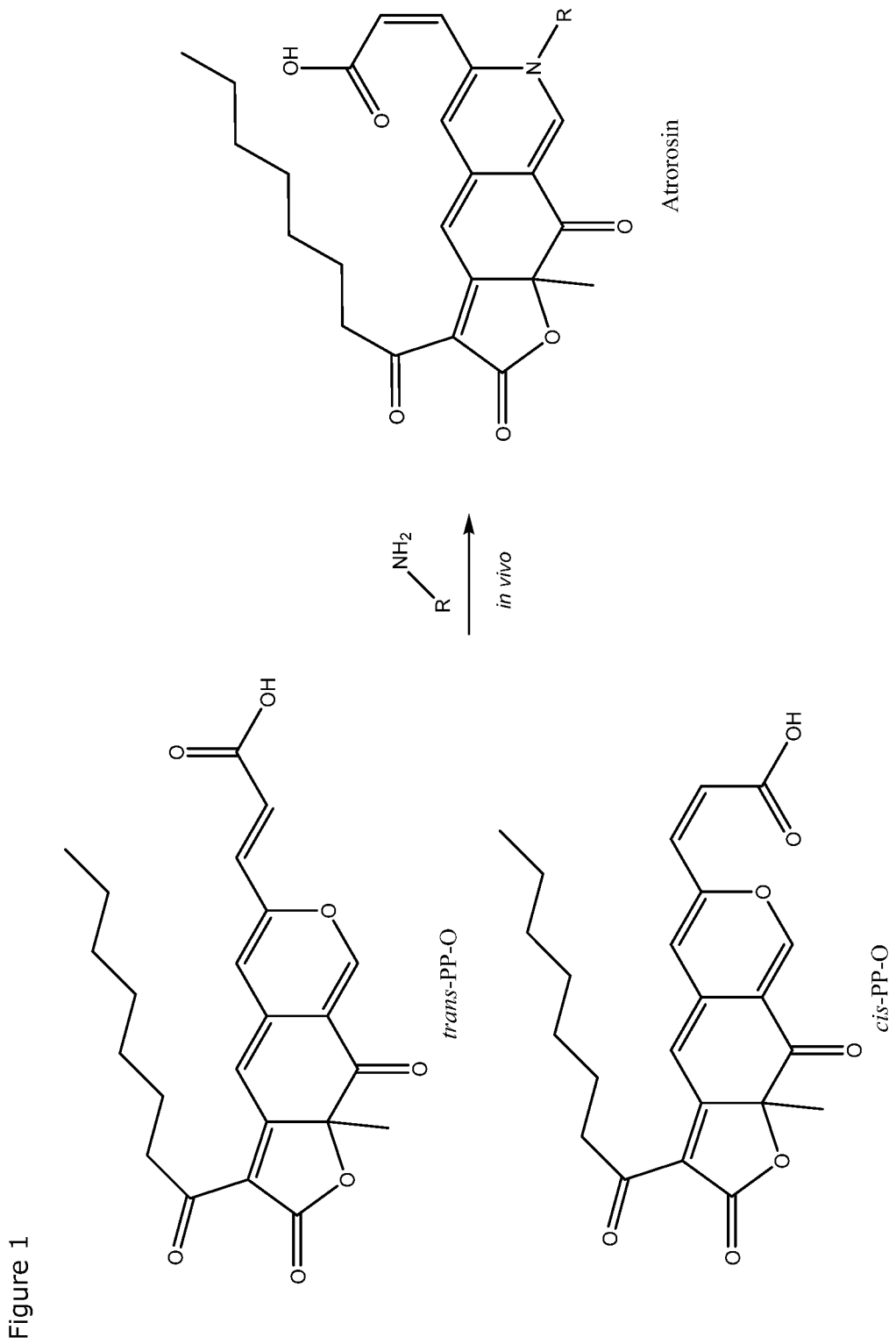

FIG. 1. Chemical structure of an atrorosin pigment, wherein R is selected from among an amino acid, a peptide, an amino sugar and a primary amine, and the configuration of the double bond between carbon 2 and 3 is cis. In vivo it is synthesised by derivatization of the isochromene-containing azaphilone precursors, cis-PP-O and trans-PP-O, with a nitrogen-containing molecule.

FIG. 2. Graphical presentation of the absorbance spectra of purified atrorosin pigments and their corresponding standard curves:

Absorbance spectrum of pure PP-O and corresponding standard curve at 450 nm with the equation: y=54.869x.

Figures 3, 4:
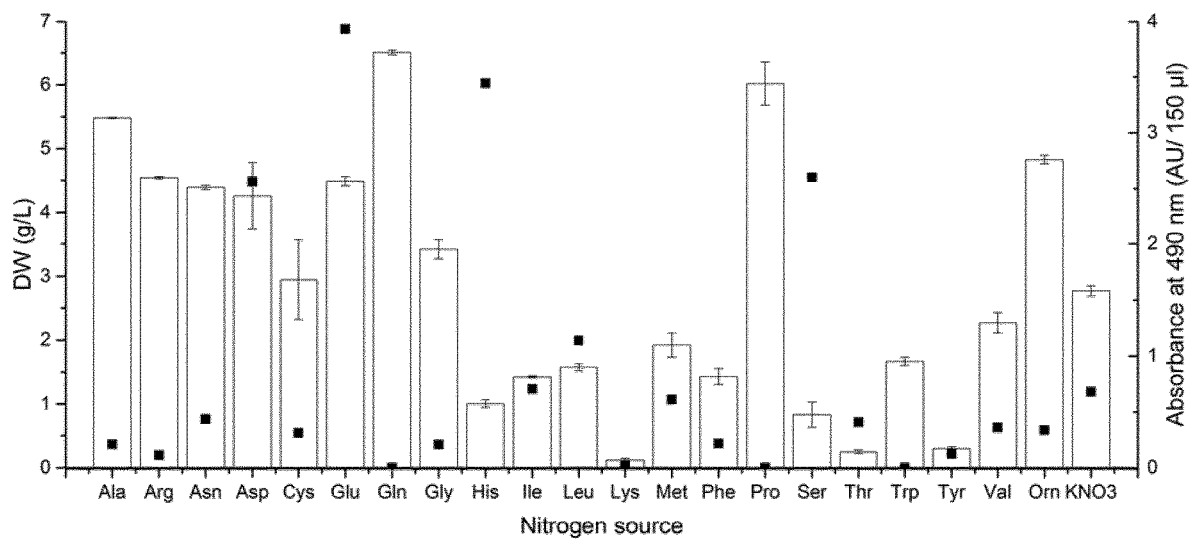

Absorbance spectrum of pure atrorosins (exemplary atrorosin-S) and corresponding standard curve at 500 nm with the equation: y=95.244x FIG. 3. Graphical presentation of biomass accumulation (bar diagram) and pigments in g/L (■) produced by one-step fermentation of $T.$ atroroseus after 96 hrs, when cultured in shake flasks in a defined fermentation medium (see Example 1.2) when supplemented with the indicated single amino acids (0.1 M) or $KNO_3$ (0.1 M) as sole nitrogen source. Samples were taken after 96 hrs. The data set is based on shake flask fermentations carried out in triplicate.

FIG. 4. Diagram showing UV-Chromatograms (measured at 520±20 nm) of compounds extracted from fermentation broth derived from one-step fermentation of $T.$ atroroseus (as defined in Example 1.2) wherein the growth medium (100 ml) was supplied with a single nitrogen source in the form of either potassium nitrate ($KNO_3$), aspartic acid, glutamic acid, histidine or serine as sole nitrogen source at a concentration of 0.1M. The pH of the medium was adjusted to pH 5 with aqueous NaOH and HCl. Cultivation was carried out in non-baffled shake flasks at 30° C. and 150 rpm in rotary shaking incubators. Samples were taken after 96 hrs. Shake flask experiments were carried out in triplicates.

Figure 5:
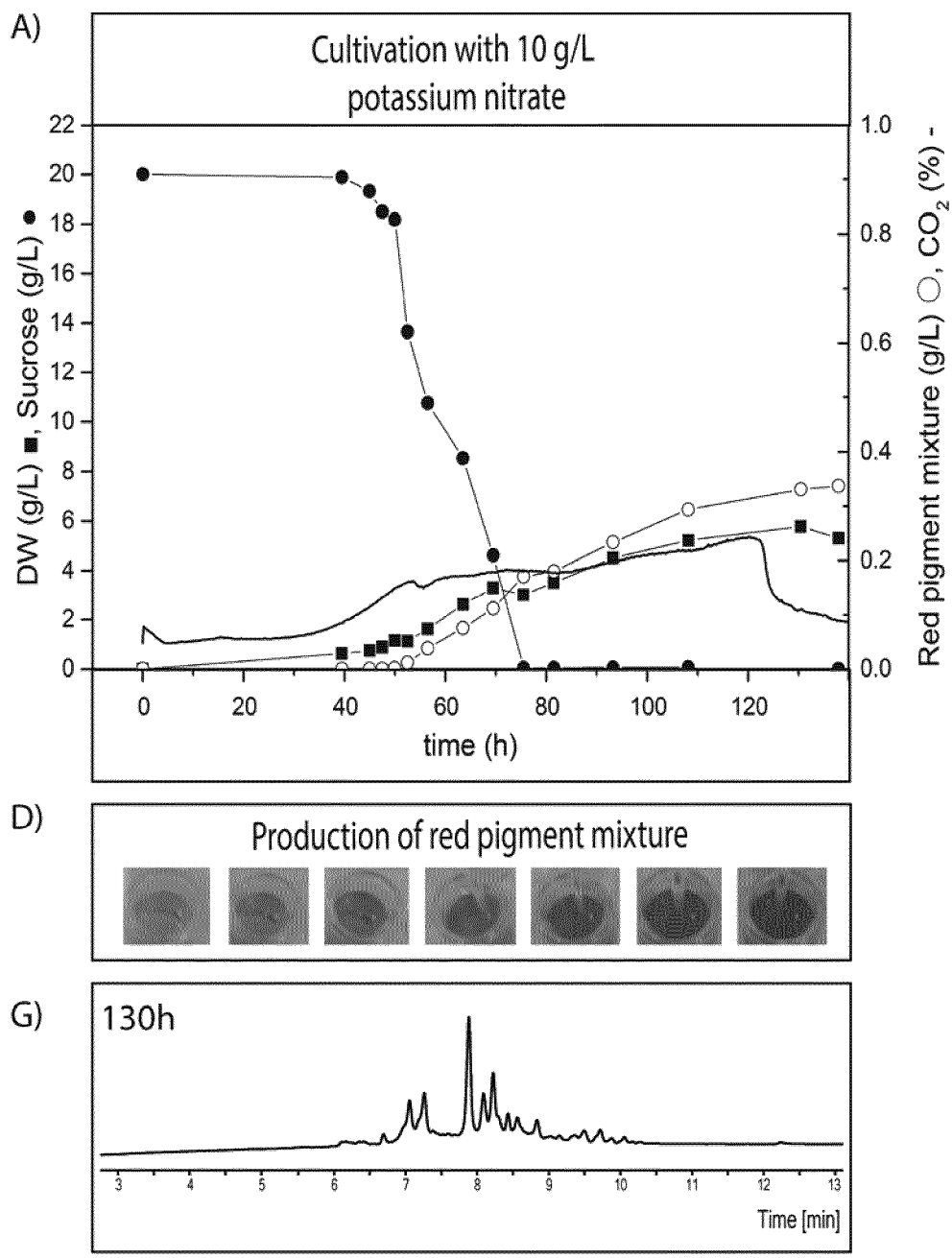
Figure 5:
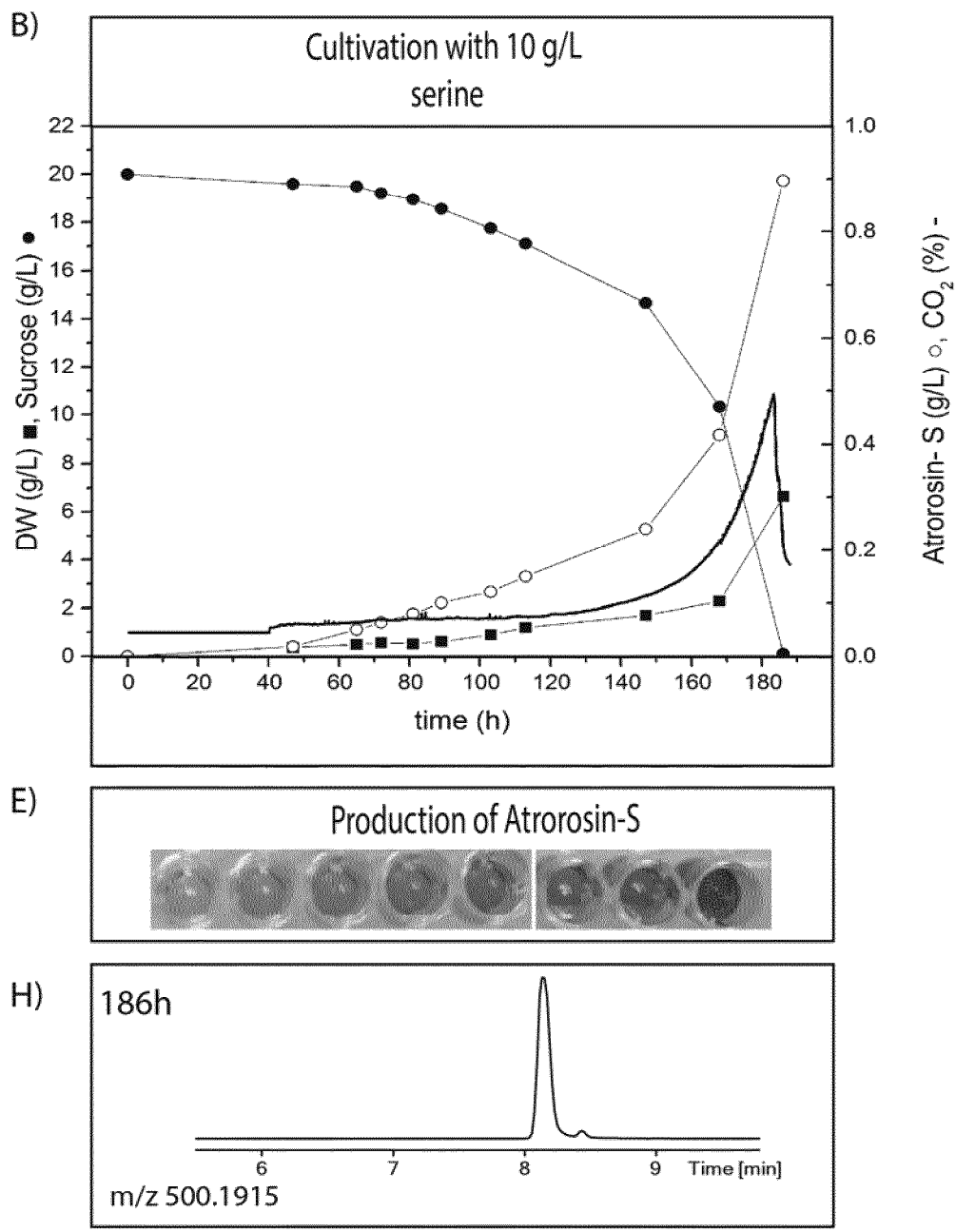
Figure 5:
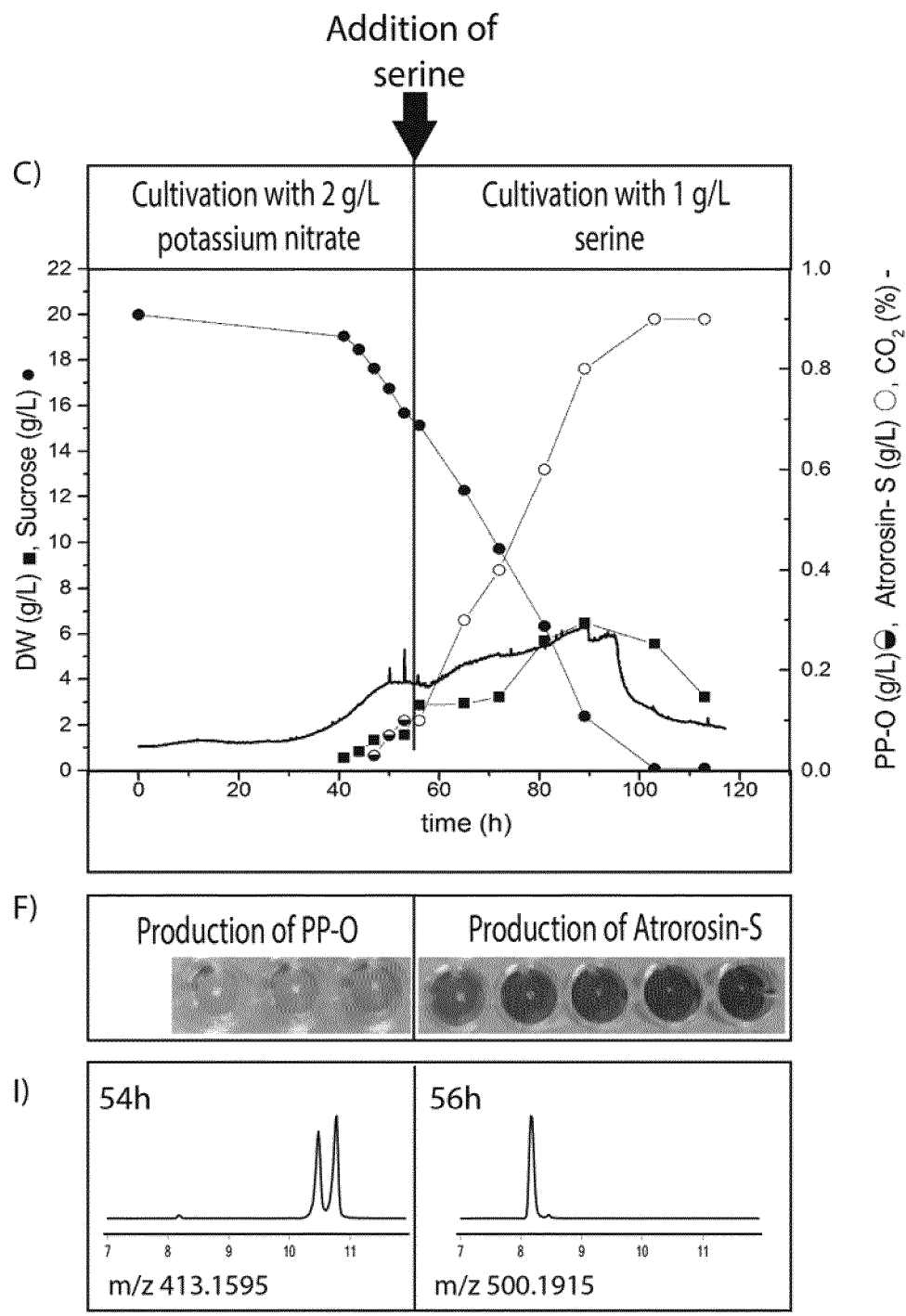

FIG. 5. Graphical presentation of biomass accumulation (DW) and levels of pigment (PP-O and atrorosin-S), $CO_2$ and sucrose detected over time during one-step or two-step fermentation of $T.$ atroroseus supplied with serine or potassium nitrate ($KNO_3$) and serine as sole nitrogen source. A) time course of one-step fermentation with 10 g/l $KNO_3$; B) time course of one-step fermentation with 10 g/l serine; C) time course of two-step fermentation; D) color profile of fermentation medium supernatant of one-step fermentation with 10 g/l $KNO_3$; E) color profile of fermentation medium supernatant of one-step fermentation with 10 g/l serine; F) color profile of fermentation medium supernatant of two-step fermentation; G) UV chromatogram (520±10 nm) of fermentation medium supernatant in one-step cultivation with 10 g/l $KNO_3$ showing a mixture of pigments; H) UV chromatogram (520±10 nm) of fermentation medium supernatant in one-step cultivation with 10 g/l serine showing atrorosin-S; and I) UV chromatogram (520±10 nm) from fermentation medium supernatant in two-step cultivation showing first formation of both cis- and trans-PP-O and then after addition of serine, essentially pure cis-atrorosin-S.

Figure 6:
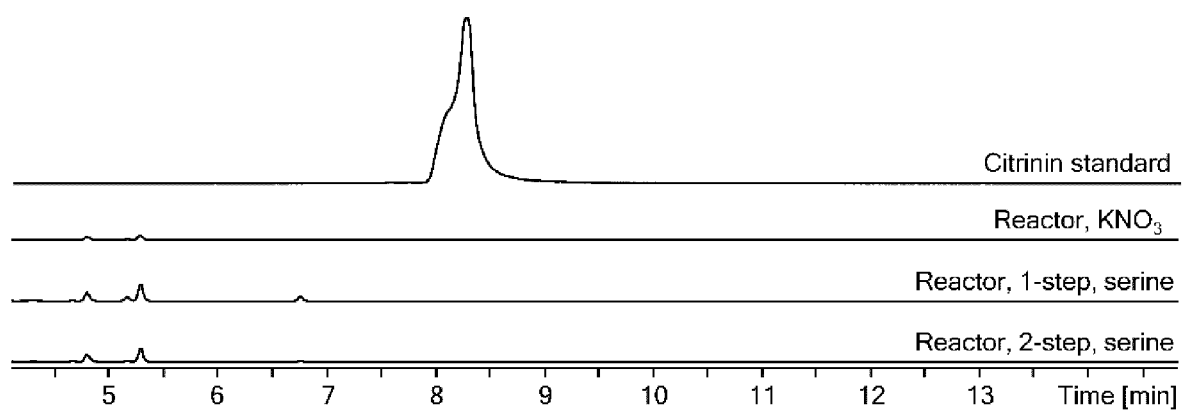

FIG. 6. Diagram showing an ion chromatogram of an authenticated standard of citrinin (m/z=251.0290) compared to chromatograms of samples of fermentation broth derived from one-step versus two-step fermentation of $T.$ atroroseus when supplied with serine as sole amino nitrogen source, as compared to potassium nitrate ($KNO_3$) as sole nitrogen source.

Figure 7:
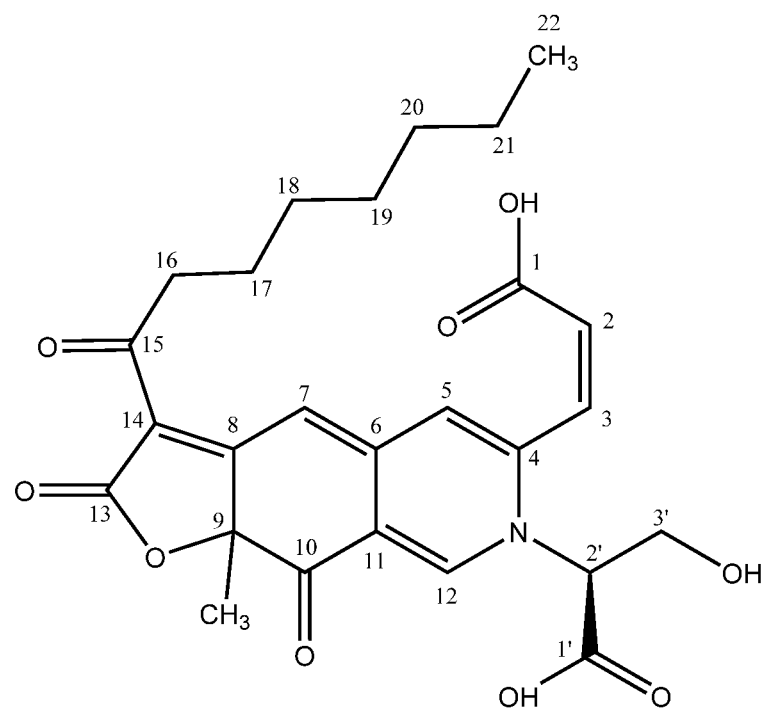

FIG. 7. Diagram showing chemical structure of cis-atrorosin-S.

FIG. 8. Diagram showing the logD values for A) atrorosin-S and monascorubramine-S and B) atrorosin-E and monascorubramine-E.

Figure 9:
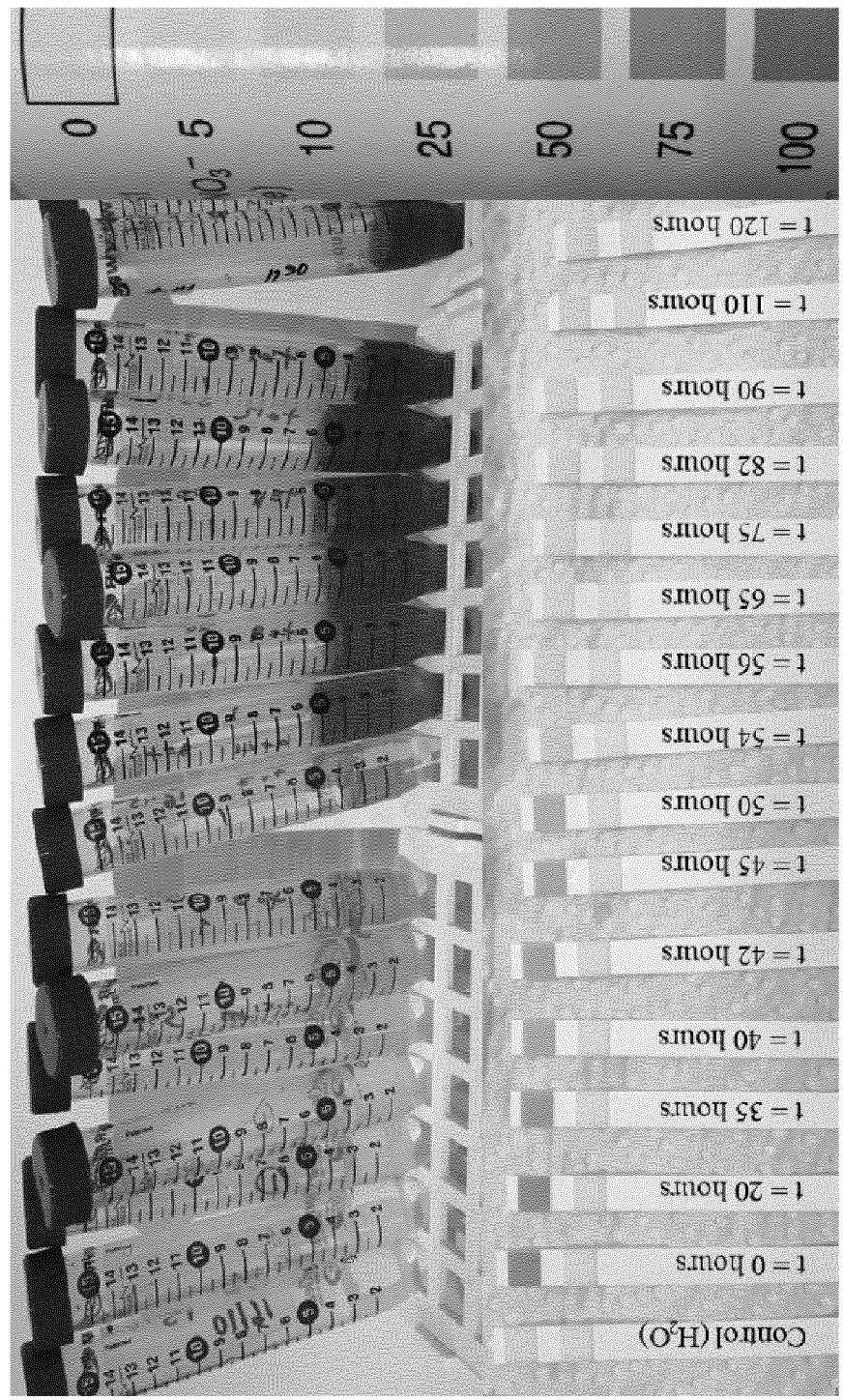

FIG. 9. Colorimetric nitrate measurements using nitrate test strips. Left top: samples taken from 2-step cultivations. Left bottom: nitrate test strips used for each sample after a 40× dilution to fit the 5-100 mg range. Sample time points are noted on the nitrate test strips FIG. 10. *Talaromyces atroroseus* cultured in bioreactor at different pH, nitrogen source $KNO_3$. A) Growth rate ($\mu$ max($h^{-1}$)) as a function of pH; B) Biomass (Ysx •) and total pigment (Ysp □) production as a function of pH.

ABBREVIATIONS AND TERMS

PP-O: is a pigment having the chemical formula $C_{23}H_{24}O_7$ and can be either in a cis- or a trans-form.

Atrorosin: is a pigment having the chemical formula $C_{23}H_{24}O_6NR$, where NR is a compound containing a primary amine, such as an amino acid, and the configuration of the double bond between carbon 2 and 3 is cis.

Growth medium essentially devoid of available inorganic nitrogen: is a growth medium which limits exponential growth and causes microbial (fungal) growth to enter a lag or cell death phase, due to lack of available nitrogen. The nitrogen source is depleted and no available nitrogen is left when the growth medium contains less than 0.5 g/L of the nitrogen source (e.g. <0.5 g/L $KNO_3$ or $NaNO_3$, such as <5 mM $NO_3^-$).

DETAILED DESCRIPTION OF THE INVENTION

The present invention provides a method for the production of individual species of azaphilone pigments by fermentation, using a fungal species belonging to the genus *Talaromyces*, preferably the species *Talaromyces atroroseus*. Species of *Talaromyces* were initially selected as potentially suitable for use as production organism since, in common with species of *Monascus*, they were found to excrete a bright red color when cultivated on solid media.

According to a first embodiment, the invention provides a method for producing an individual species of azaphilone pigment using a one-step fermentation procedure comprising:

a) providing spores or mycelia of a species of the genus *Talaromyces*,
b) cultivating said spores or mycelia in a liquid growth medium,
c) recovering the azaphilone pigment produced during cultivation in step b), and
optionally isolating one or more of said azaphilone pigments,
wherein the sole nitrogen source in said liquid growth medium in step (b) is a single compound selected from the group consisting of an amino acid, a peptide, an amino sugar and any other primary amine; and wherein the atrorosin pigment has the structure of Formula I:

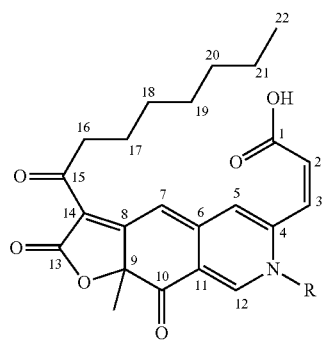

wherein N—R is selected from the group consisting of an amino acid, a peptide, an amino sugar and a primary amine, and the configuration of the double bond between carbon 2 and 3 is cis.

A suitable sole nitrogen source includes an amino sugar such as glucosamine or galactosamine; and includes a primary amine such as anthranilic acid, aniline or p-phenylenediamine.

Preferably, the sole nitrogen source is a single amino acid, selected from one of the group consisting of: L-alanine, L-arginine, L-asparagine, L-aspartate, L-cysteine, L-glutamine, L-glutamate, L-glycine, L-histidine, L-isoleucine, L-leucine, L-lysine, L-methionine, L-phenylalanine, L-serine, L-threonine, L-tyrosine, L-valine and L-ornithine.

The liquid growth medium, comprising a nitrogen source, is a synthetic medium comprising salts, trace metals, and a source of carbon. A suitable source of carbon includes glucose, sucrose, maltose, soluble starch, beet or cane molasses, malt and any combination of at least two thereof.

The growth medium preferably comprises or consists of the following salts and trace metals: $KH_2PO_4$ (for example 1 g/L), NaCl (for example 1 g/L), $MgSO_4.7H_2O$ (for example 2 g/L), KCl (for example 0.5 g/L), $CaCl_2.H_2O$ (for example 0.1 g/L) and a trace metal solution (for example 2 mL/L). The trace metal solution may comprise, or consist, of: $CuSO_4.5\ H_2O$ (for example 0.4 g/L), $Na_2B_4O_7.10\ H_2O$ (for example 0.04 g/L), $FeSO_4.7\ H_2O$ (for example 0.8 g/L), $MnSO_4.H_2O$ (for example 0.8 g/L), $Na_2MoO_4.2\ H_2O$ (for example 0.8 g/L), $ZnSO_4.7\ H_2O$ (for example 8 g/L). The concentration of the compound providing the sole nitrogen source in the growth medium may be from 0.05M to 1M, for example at least 0.05, 0.075, 0.10, 0.125, 0.15, 0.175, 0.2, 0.3, 0.4, 0.5, 0.6, 0.7, and 0.8M.

The pH of the growth medium provided and maintained during step (b) is preferable between 4 and 6; more preferably between 4.5 and 5.5; where the pH may be adjusted by the addition of aqueous NaOH or HCl.

Cultivation in step (b) may be performed by suspending spores or mycelia of the species of the genus *Talaromyces* in the liquid growth medium; or more preferably by submerging spores or mycelia of the species of the genus *Talaromyces* in the liquid growth medium.

The spores in step (a) may comprise an aqueous suspension of spores of the species of the genus *Talaromyces*. Preferably, the species of the genus *Talaromyces* is the species *Talaromyces atroroseus* (for example the strain *Talaromyces* atroroseus IBT 11181).

According to a second embodiment, the invention provides a method for producing an individual species of azaphilone pigment using a modification of the one-step fermentation procedure, called the two-step fermentation procedure. According to this modification, an additional step (a') is performed after step (a). In step (a'), the spores or mycelia provided in step (a) are cultivated in a preliminary liquid growth medium, wherein the sole nitrogen source is an inorganic nitrogen source and the concentration of $NO_3^-$ is no more than 20 mM. The inorganic nitrogen source may be selected from the group consisting of: $KNO_3$ and $NaNO_3$.

The preliminary liquid growth medium, comprising the inorganic nitrogen as sole nitrogen source, is a synthetic medium comprising salts, trace metals, and a source of carbon. The composition of this synthetic medium with respect to salts and trace metals is: $KH_2PO_4$ (for example 1 g/L), NaCl (for example 1 g/L), $MgSO_4.7H_2O$ (for example 2 g/L), KCl (for example 0.5 g/L), $CaCl_2.H_2O$ (for example 0.1 g/L) and a trace metal solution (for example 2 mL/L). The trace metal solution may comprise, or consist of: $CuSO_4.5\ H_2O$ (for example 0.4 g/L), $Na_2B_4O_7.10\ H_2O$ (for example 0.04 g/L), $FeSO_4.7\ H_2O$ (for example 0.8 g/L), $MnSO_4.H_2O$ (for example 0.8 g/L), $Na_2MoO_4.2\ H_2O$ (for example 0.8 g/L), $ZnSO_4.7\ H_2O$ (for example 8 g/L. A suitable source of carbon includes glucose, sucrose, maltose, soluble starch, beet or cane molasses, malt and any combination of at least two thereof.

According to the two-step fermentation method, cultivation of the *Talaromyces* culture produced in step (a') is then continued with a further cultivation step (b) in a liquid growth medium. The liquid growth medium in step (b) is a synthetic medium having the same composition with respect to salts and trace metals as the preliminary liquid growth medium. However, the liquid growth medium in step (b) comprises a compound selected from one of an amino acid, a peptide, an amino sugar and a primary amine, as a sole source of organic nitrogen. Suitable organic nitrogen sources are selected from the group consisting of an amino acid, a peptide, an amino sugar and any other primary amine; and correspond to suitable sources used in the liquid growth medium in the one-step fermentation procedure. Although a source of inorganic nitrogen is a component of the preliminary liquid growth medium in step (a'); no additional source of inorganic nitrogen is included in the liquid growth medium in step (b), but instead the inorganic nitrogen is substituted with the given sources of organic nitrogen.

Two-step fermentation, according to the second embodiment, may be performed by cultivating the spores or mycelium in the preliminary liquid growth medium in step (a'), and then adding in step (b) the sole source of organic nitrogen to the culture produced by step (a'). The inorganic nitrogen content of the preliminary liquid growth medium is depleted during cultivation of the fungal spores or mycelium in step (a'), such that the growth medium is essentially devoid of available inorganic nitrogen at the end of step (a'). The inorganic nitrogen content of the preliminary liquid growth medium can be adjusted to ensure complete depletion by the end of step (a'); for example by providing no more than 2 g/L, 1.75 g/L, 1.5 g/L, 1.25 g/L, 1 g/L of KNO$_3$ or NaNO$_3$, such as providing no more than 20 mM, 17.5 mM, 15 mM, 12.5 mM, 10 mM of NO$_3^-$ Once the level of inorganic nitrogen present in the preliminary liquid growth medium is depleted to an amount of less than 0.5 g/L, 0.4 g/L, 0.3 g/L, 0.2 g/L, 0.1 g/L, or 0.05 g/L of either KNO$_3$ or NaNO$_3$, such as depleted to an amount of less than 5 mM, 4 mM, 3 mM, 2 mM, 1 mM, 0.5 mM of NO$_3^-$, then it is no longer able to support growth of the Talaromyces culture.

Alternatively, the preliminary liquid growth medium in step (a') is replaced by the liquid growth medium comprising the above identified organic nitrogen compound as sole nitrogen source, at the start of the further cultivation step (b).

The pH of the growth medium provided in step (a') and maintained during step (b) is preferable between 4 and 6; preferably between 4.5 and 5.5; where the pH may be adjusted by the addition of aqueous NaOH or HCl.

The cultivation conditions during one-step and two-step fermentation support aerobic metabolism in the *Talaromyces* culture. Aerobic metabolism relies on a sufficient aeration, which can be achieved by shaking the liquid culture or by supplying a source of air (e.g. oxygen).

The one-step and two-step fermentation procedure can be performed in a bioreactor. The liquid growth media (described above) used in both the one-step and two-step fermentation procedure may be supplied to the bioreactor to facilitate either batch, fed-batch or continuous culture of the fungal culture.

The duration of the cultivation steps (a') and (b) in the two-step fermentation procedure are selected to optimise growth of the *Talaromyces* culture (as measured by biomass) and the yield of azaphilone pigment produced by the *Talaromyces* culture. The cultivation step (a') is preferably at least 28 h; for example between 30 h and 40 h. The cultivation step (a') may be about 32, 34, 36, 38, 40, 42, 44, 46, 48, 50, 52 and 54 h in duration. The duration of the cultivation step (b), that follows step (a'), is preferably at least 50 h; for example between 50 h and 80 h. The cultivation step (b) may be about, 50, 52, 54, 56, 58, 60, 62, 64, 66, 68, 70, 75, 80, h in duration.

The azaphilone pigment produced by the cultivation of the *Talaromyces* culture, according to the first or second embodiment, is extracellular and can therefore be recovered from the liquid medium. Surprisingly, the onset of azaphilone pigment synthesis takes place after significantly fewer hours of cultivation when the two-step fermentation procedure is used as compared to the one-step fermentation procedure (see Example 3.2; FIG. 5). Additionally, the carbon economy of the two-step fermentation procedure, as judged by azaphilone pigment yield, is superior (see Example 3.4-3.5; Table 3 and 4).

Strains of *Talaromyces atroroseus* are reported to be capable of producing a mixture of *Monascus* pigments, including a yellow azaphilone (PP-Y), and the cis- and trans-isomers of an orange azaphilone (PP-O) and a violet azaphilone (PP-V). Surprisingly, the azaphilone pigment produced by the method according to the first and second embodiments of the invention is a single species of atrorosin pigment and not a mixture of pigments (see Example 2). When KNO$_3$ or NaNO$_3$ (in low amounts e.g. 2 g/L (0.02M NO$_3^-$)) is provided as the sole source of nitrogen during step (a') of the two-step fermentation procedure, this selectively promotes the synthesis of low amounts of both cis-and trans-forms of the orange azaphilone pigment (PP-O) during step (a'). In subsequent step (b), the amino-group present in the source of organic nitrogen is incorporated into the PP-O azaphilone core isomeric structures (cis- and trans-PP-O) to form the specific cis-atrorosin derivative in essentially pure form (FIG. 1). Thus the single species of atrorosin pigment produced by the method can be extracted and recovered without the need for multiple and possibly complex purification steps. Furthermore, the products of the fermentation using the method are free of any mycotoxin (see Example 4), and are therefore safe for human use.

According to a third embodiment, the invention provides a novel atrorosin pigment having the formula I:

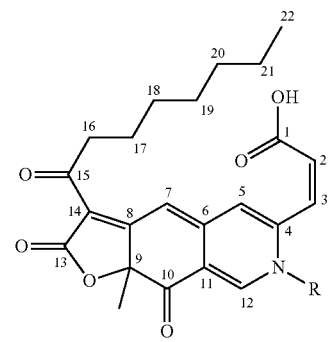

wherein N—R is selected from among an amino acid, a peptide, an amino sugar (e.g. glucosamine or galactosamine) and a primary amine (e.g. anthranilic acid, aniline or p-phenylenediamine), and the configuration of the double bond between carbon 2 and 3 is cis.

In a preferred embodiment, the atrorosin pigment has formula I, wherein N—R is an amino acid selected from one of the group consisting of: L-alanine, L-arginine, L-asparagine, L-aspartate, L-cysteine, L-glutamate, L-glycine, L-histidine, L-isoleucine, L-leucine, L-lysine, L-methionine, L-phenylalanine, L-serine, L-threonine, L-tyrosine, L-valine and L-ornithine.

This novel atrorosin having formula I, as defined above, is the azaphilone pigment that is recovered from the fungal culture produced by the fermentation procedure according to the first or second embodiment of the invention. The yield of this novel atrorosin using this fermentation procedure is at least 4-fold higher than the combined sum of different atrorosins produced, when the fungal strain is cultivated under the same conditions but supplied with a synthetic medium with inorganic nitrogen as sole nitrogen source (see Example 3.4).

An important property of the novel atrorosin having formula I is its increased water solubility when compared to the known *Monascus* pigments. This is due to the carboxylic acid in the backbone structure in the atrorosins and the polarity conferred by the incorporated amino containing moieties (see Example 6.1).

Methods for extracting and detecting an atrorosin having formula I are detailed in Examples 2.1 and 2.2. The chemical structure of an atrorosin having formula I can be determined by means of Ultra-high Performance Liquid Chromatography coupled to Diode Array Detection and High Resolution Mass Spectrometry and Nuclear magnetic resonance spectroscopy, as described in Examples 5.1 and 5.2.

An atrorosin having formula I can be used as a coloring agent in a food product, a non-food product and a cosmetic. The food product may be selected from among the following foods: baked good, baking mix, beverage and beverage base, breakfast cereal, cheese, condiment and relish, confection and frosting, fat and oil, frozen dairy dessert and mix, gelatin, pudding and filling, gravy and sauce, milk product, plant protein product, processed fruit and fruit juice, and snack food.

The non-food product may be selected from among the following non-foods: textile, cotton, wool, silk, leather, paper, paint, polymer, plastic, inks, tablet.

The cosmetic product may be in the form of a free, poured or compacted powder, a fluid anhydrous greasy product, an oil for the body and/or the face, a lotion for the body and/or the face, or a hair product.

The invention provides a kit for coloring a product, wherein the kit comprises at least one atrorosin pigment having formula I according to the invention; wherein the pigment is supplied in a container (optionally combined with a dispensing agent e.g. colloid or thickening agent), wherein the product is selected from among a food, a non-food product and a cosmetic.

EXAMPLES

Example 1

Production of Atrorosins, a Novel Class of Azaphilone Pigments, by Fermentation 1.1 Strain Maintenance and Spore Production The fungal strain, *Talaromyces atroroseus* IBT 11181 (IBT DTU strain collection), was used for production of atrorosins. Spores of *T. atroroseus* were propagated on plates on Czapek Dox Agar (CYA) agar (supplied by 70185 Sigma-Aldrich) and incubated at 30° C. for 7 days. Spores were harvested with 0.9% sodium chloride (NaCl) solution. The suspension was filtered through mira-cloth to separate spores from mycelia. The spore solution was centrifuged for 10 min at 10,000 rpm at 4° C. The supernatant was removed and the spore pellet was re-suspended in 0.9% NaCl solution. The spore concentration was determined by using a Burker-Turk counting chamber. All cultivations were inoculated to give an initial spore concentration of $10^6$ spores/ml.

1.2 One-Step Fermentation Procedure for Production of Atrorosins

Small scale production: Atrorosins were produced by a one-step fermentation using a fermentation medium comprising the following components: sucrose (7.5 g/L), glucose (0.375 g/L), $KH_2PO_4$ (1 g/L), NaCl (1 g/L), $MgSO_4.7H_2O$ (2 g/L), KCl (0.5 g/L), $CaCl_2.H_2O$ (0.1 g/L) and trace metal solution (2 mL/L). The trace metal solution consisted of $CuSO_4.5 H_2O$ (0.4 g/L), $Na_2B_4O_7 .10 H_2O$ (0.04 g/L), $FeSO_4.7 H_2O$ (0.8 g/L), $MnSO_4.H_2O$ (0.8 g/L), $Na_2MoO_4 .2 H_2O$ (0.8 g/L), $ZnSO_4.7 H_2O$ (8 g/L). Various nitrogen sources were supplied, by providing: 0.1 M of an L-amino acid selected from L-alanine, L-arginine, L-asparagine, L-aspartate, L-cysteine, L-glutamine, L-glutamate, L-glycine, L-histidine, L-isoleucine, L-leucine, L-lysine, L-methionine, L-phenylalanine, L-proline, L-serine, L-threonine, L-tryptophan, L-tyrosine, L-valine and L-ornithine. The pH of the medium was adjusted to pH 5 with aqueous NaOH and HCl. Fermentation, in a volume of 100 ml, was carried out in non-baffled shake flasks at 30° C. and 150 rpm in rotary shaking incubators. Samples were taken after 96 hrs. Shake flask experiments were carried out in triplicates. As control/benchmark, $KNO_3$ (0.1M) was tested as nitrogen source instead of the amino acids.

Large scale production: Atrorosins were also produced by one-step fermentation in a 1 L bioreactor, using the same medium, with the modification that the medium comprised 20 g/L sucrose and serine as sole nitrogen source and at pH of 4.5. The fermentation was performed at 30° C., 800 rpm, and 1 vvm. The bioreactor experiments were carried out in duplicates.

1.3 Analysis of *T. atroroseus* Biomass Obtained by Fermentation

*T. atroroseus* biomass accumulated during fermentation was measured as dry weight (DW) using pre-weighed filters. The filters were pre-dried in a microwave for 20 min, kept in a desiccator for a minimum of 10 min and weighed. For DW measurement, the filters were placed in a vacuum filtration pump and ca. 10 ml of the fermented culture was added. Subsequently the filters with the biomass were dried in a microwave for 20 min and kept in a desiccator for a minimum of 10 min before being re-weighed. The weight of the biomass was determined as the difference of the filter weight before and after sample application, and assuming a culture broth density of 1 g/L.

1.4 Quantitative Analysis of Atrorosins Produced by Fermentation

The absorbance values of the pigments were determined using a Synergy 2 photo spectrum and a 96 well microliter plate. 150 μl samples of filtered fermentation broth, derived from fermentation on medium comprising each of the amino acids as nitrogen source, were scanned in the range of 200-700 nm and maximum absorbance values were determined. Absorbance at 490 nm indicated presence of red pigments. A standard curve of an orange and red pigment was used to calculate the concentration in the medium (see FIG. 2).

1.5 Atrorosin Pigments and Biomass Produced by Fermentation of *T. atroroseus* on Defined Fermentation Medium The essential role of the source of amino nitrogen on the production of pigments by *T. atroroseus* and biomass accumulation during one-step fermentation was assessed for each of the 20 natural amino acids and the non-proteinogenic amino acid ornithine in a defined medium as defined in Example 1.2 in small scale shake flasks. As a control, fermentation was performed in defined medium using $KNO_3$ as sole nitrogen source.

The concentration of pigment produced in each fermentation was determined by measuring the absorbance at 500 nm of the entire fermentation broth from which the pigment concentration was calculated using the standard curve shown in FIG. 2.

As seen in FIG. 3, although each natural amino acid supported growth when supplied as sole nitrogen source, some amino acids favoured biomass accumulation more than others. Biomass accumulation was highest with proline (6.05+0.3 g/L), followed by alanine (5.48+0.01 g/L) and ornithine (4.83+0.07 g/L). Arginine (4.45+0.02 g/L), asparagine (4.4+0.03 g/L), aspartic acid (4.26+0.5 g/L) and glutamic acid (4.49+0.24 g/L) also lead to high biomass values. The control supplied with $KNO_3$ as nitrogen source yielded 2.77±0.06 g/L. Histidine, isoleucine, leucine, lysine, methionine, phenylalanine, serine, threonine, tryptophan and tyrosine supported low biomass values below 2 g/L.

In terms of pigment production, the amino nitrogen source giving the highest yields was glutamic acid, with a yield of 0.39 g/L. Other high yielding amino nitrogen sources were aspartic acid (0.25 g/L), histidine (0.19 g/L) and leucine (0.11 g/L), followed by serine (0.08 g/L) and isoleucine (0.07 g/L) (see FIG. 3).

No detectable pigment production was observed when providing proline as sole amino nitrogen source. This is believed to be due to the secondary amine in proline, preventing its incorporation into the core structure of the pigment. The other 17 natural amino acids are incorporated via their primary amine. In the absence of pigment formation, T. atroroseus is seen to use proline as a carbon source for growth, leading to the observed high accumulation of biomass.

The relatively lower pigment production in medium comprising glutamine and asparagine is attributed to a failure to maintain a stable pH in shake flasks. The pH of the fermentation broth after 72 hrs, in medium comprising glutamine dropped to pH 3.8, while medium comprising glutamic acid had a final pH of 6.1 (see Table 1).

TABLE 1 pH of fermentation broth after 72 h fermentation in shake flasks

| Amino acid source | Broth PH |
|---|---|
| Gln | 3.7 |
| Glu | 6.1 |

Bioreactor experiments for the 1-step method demonstrated that the pH of the fermentation liquid greatly affected pigment and biomass production.

FIG. 10A shows that the growth rate of Talaromyces atroroseus IBT 11181 was significantly higher when cultivated at a low pH (such as pH 3-4.5) compared to higher pH (such as pH 5-7). However, as shown in Table 2 and FIG. 10B, when the pH of the fermentation liquid was maintained at pH 3, this completely hindered pigment production. Also at high pH (such as pH≥6), essentially no pigment production was observed. As already seen from shake flask cultures lacking pH control, the bioreactor experiments confirmed the importance of pH control for maintaining conditions favourable for pigment production.

TABLE 2

Effect of pH on pigment yield in bioreactor

| | Total pigment yield g/g of Sucrose | |
|---|---|---|
| N-source* | 0.1M KNO$_3$ | 0.1M (NH$_4$)$_2$SO$_4$ |
| pH 3 | No color secretion | |
| pH 4 | 0.009 ± 0.001 | 0.003 ± 0.001 |
| pH 4.5 | 0.010 ± 0.001 | n.a. |
| pH 5 | 0.006 ± 0.001 | 0.009 ± 0.013 |

*Growth medium as defined in Example 1.2; wherein the sole nitrogen source is as indicated.

Example 2

High Purity Single Atrorosin Pigments are Obtained by Fermentation of T. atroroseus on Defined Fermentation Medium Samples collected from fermentation cultures were first filtered through a sterile Statorius Stedim filter with a pore size of 0.45 μm in order to separate biomass from the filtrate prior to their analysis by HPLC, absorbance and LC-MS. Two methods were used for the purification of atrorosins produced by fermentation of T. atroroseus on defined fermentation medium.

2.1 Extraction and Purification of Atrorosins Produced by Fermentation

Method I: Fermentation broth derived from the cultivation of Taleromyces atroroseus (IBT 11181) was filtered, centrifuged, and the supernatant was extracted twice with 1:1 ethyl acetate (EtOAc) at pH 3, adjusted with formic acid (FA). The organic extracts were concentrated in vacuo. The target compound was enriched into a crude fraction by flash chromatography of the EtOAc extract, on an Isolera One automated flash system (Biotage), using a water/methanol gradient elution on C18 column material. The final isolation was performed on a semi-preparative HPLC, a Waters 600 Controller with a 996 photodiode array detector, equipped with a LUNA II C18 column (250 mm×10 mm, 5 μm, Phenomenex) using a water/acetonitrile gradient with 50 ppm triflouroacetic acid (TFA).

Method II: Fermentation broth derived from the cultivation of Taleromyces atroroseus (IBT 11181) was filtered, centrifuged and the filtrate was extracted three times, with ⅓ volume of EtOAc, at pH 3 (adjusted with FA). The combined EtOAc phases were evaporated to 100 mL and extracted twice with milli-Q water (1:1) at pH 8 (adjusted with ammonium hydroxide). The water phase was re-adjusted to pH 3 with FA and extracted two time with EtOAc, followed by evaporation, to yield a highly enriched >95% pigment fraction (a mixture of several atrorosins and N-amino acid monascorubramine, ratio>10:1). The pigments were separated on a Gilson 332 semi-prep HPLC system equipped with a Gilson 172 diode array detector, using a LUNA II C18 column (250 mm×10 mm, 5 μm, Phenomenex), with a water/acetonitrile gradient.

2.2 Quantitative Analysis of Atrorosins Produced by Fermentation

The absorbance values of the individual pigment solutions were determined using a Synergy 2 photo spectrum and a 96 well microtiter plate. 150 μl of sample broth of each amino-acid-pigment-solution were scanned in the range of 200-700 nm and maximum absorbance values were determined. Absorbance at 490 nm indicates presence of red pigments. A standard curve of an orange and red pigment can be used to calculate the concentration in the medium (see FIG. 2).

2.3 Single Atrorosin Pigments Detected in Fermentation Broth of T. atroroseus Fermented on Defined Medium The enrichment of a given azaphilone produced by fermentation of T. atroroseus is greatly increased by providing a single amino acid as sole nitrogen source (FIG. 4). When T. atroroseus was cultivated with 0.1M potassium nitrate as nitrogen source, a plethora of different azaphilone pigments were detected, while when only a single amino acid was supplied as the sole nitrogen source, only one major UV-detectable peak corresponding to the atrorosin incorporating this particular amino acid into its structure, was observed (FIG. 4).

Example 3

Large Scale Production of High Purity Single Atrorosin Pigments by Fermentation of *T. atroroseus* on Defined Fermentation Medium

3.1 A Two-Step Fermentation Procedure for Production of Atrorosins

Two-Step Cultivation: Two-step fermentation was carried out in 1 L bioreactors. The fermentation medium contained sucrose (20 g/L), glucose (1 g/L), $KH_2PO_4$ (10 g/L), NaCl (1 g/L), $MgSO_4 \cdot 7 H_2O$ (2 g/L), KCl (0.5 g/L), $CaCl_2 \cdot H_2O$ (0.1 g/L) and trace metal solution (2 mL/L). In the first step, the medium comprised 2 g/L (0.02M) of $KNO_3$ as sole nitrogen source. After 53 h of cultivation, serine was added to a final concentration of 1 g/L (0.01M) to induce formation of the amino acid derivative. The fermentation conditions were maintained at 30° C., 800 rpm, 1 vvm and a pH 4.5.

3.2 Faster Atrorosin Production Using Two-Step Fermentation Procedure Instead of One-Step Fermentation Both biomass yield and pigment production by *T. atroroseus* using the one-step and two-step fermentation procedures were compared. In the one step-fermentation, 0.1M serine was used as the sole nitrogen source and 0.1M $KNO_3$ was used as control. In the two-step fermentation, cis- and trans-PP-O production was initially induced by 0.02M $KNO_3$ which was then converted into cis-atrorosin-S by the addition of L-serine (in final concentration 0.01M), after $KNO_3$ was depleted from the growth medium.

During one-step fermentation, fermentation became carbon limiting for the control ($KNO_3$ as sole nitrogen source) after 75 h, and at the end of fermentation yielded 0.35 g/L of mixed pigments and 5 g/L of biomass (see FIG. 5A). During cultivation, pigment production changed colour from orange (PP-O) to red (mixture of atrorosins and monascus pigments) as carbon was depleted (FIGS. 5A&D).

During one-step fermentation with L-serine as sole nitrogen source, the fermentation became carbon limiting after 180 h, and at the end of fermentation yielded 0.9 g/L of cis-atrorosin-S and 6.5 g/L of biomass (see FIG. 5B). Similar results were obtained for other natural amino acids (see FIG. 4). The cis-atrorosin-S production increased with fungal growth during the entire time course of the fermentation and no PP-O isomers were observed (FIGS. 5B&E).

In the two-step fermentation procedure, a low amount of $KNO_3$ (20 mM) was initially supplied as the nitrogen source, resulting in the biosynthesis of the orange pigment, PP-O (FIGS. 5C&F). An amino acid (in this case serine), at a concentration 0.01M, was first added after 53 h fermentation, which was subsequently incorporated into the cis- and trans-PP-O azaphilone core structures, resulting in the synthesis of the red pigment, cis-atrorosin S (FIG. 1). While the two-step cultivation also yielded 0.9 g/L of atrorosin S, but a higher biomass of 7.4 g/L of biomass, as compared to 6.5 g/L, this was obtained after only 100 h at the onset of carbon limitation.

3.3 Identification of the Atrorosin Pigments Produced by Fermentation of *T. atroroseus*

The UV chromatogram profiles (520±20 nm) of the atrorosin pigments produced by one-step fermentation of *T. atroroseus* on defined fermentation medium comprising either $KNO_3$ or serine as sole nitrogen source are shown in FIGS. 5G & H, respectively, while the pigment profile of the two-step fermentation just before and after amino acid addition is shown in FIG. 5I.

The fermentation comprising 0.1M $KNO_3$ as sole nitrogen source produced a mixture of pigments (FIG. 5G), while the fermentation comprising 0.1M L-serine as sole nitrogen source produced cis-atrorosin-S with minimal impurities (FIG. 5H).

For the two-step fermentation, during the first phase (low $KNO_3$ amounts) two isomers of PP-O were produced: in the second phase (after addition of serine), both isomers of PP-O were converted into cis-atrorosin-S.

The major UV peak detected at 8 minutes in both chromatograms H and I corresponds to atrorosin-S (as confirmed by mass spectrometry) and the two peaks detected between 10 and 11 minutes in chromatogram I corresponds to the cis- and trans-isomers of PP-O.

3.4 Nitrate Depletion During Two-Step Fermentation

After 54 hours, it was estimated that $KNO_3$ was depleted due to the plateau in the exhaust in $CO_2$ and biomass (FIG. 5C). This was confirmed by semi-quantitative estimation using Quanto-fix nitrate strips as shown in FIG. 9. Already after 42 hours the nitrate levels started to drop in comparison to earlier in the fermentation; this corresponds to when the two isomeric forms of the precursor PP-O started to be produced (FIG. 5C). What was more evident was that after the switch to serine as nitrogen source, the pigments in the supernatent turned vibrant red, and as evidenced by the nitrate quanto-strips, nitrate was depleted.

For the production of a single atrorosin pigment by *T. atroroseus* according to the 2-step fermentation method it is essential that nitrate levels in the culture medium are depleted (to less than 5 mM) prior to the addition of an amino acid.

Culturing *T. atroroseus* in a fermentation medium comprising high nitrate concentrations (such as >0.02M), a mixture of pigments is produced (as seen in FIGS. 5A and G) prior to nitrate depletion and as a consequence, when an amino acid is added to the cultivation medium, it is not possible to obtain a single pure atrorosin product.

Culturing *T. atroroseus* in a fermentation medium comprising low nitrate levels (such as <0.02M) and adding an amino acid to the cultivation medium "too soon" i.e. before nitrate depletion and before the onset of PP-O accumulation, a single atrorosin product is not obtained but rather a mixture of pigments. When added before the onset of PP-O production, the amino acid is utilized for cellular functions and will not be present in excess (compared to nitrate), resulting in a mixture of atrorosins.

3.5 Carbon Economy of Atrorosin Production is Enhanced Using Two-Step Fermentation (Calculation Referred to Table 3)

In the one-step fermentation procedure supplied with serine, *T. atroroseus* uses 20 g/L of sucrose and 10 g/L of serine to produce 0.9 g/L of atrorosin-S.

In the two-step fermentation procedure *T. atroroseus* uses 20 g/L of sucrose and 2 g/L of serine to produce 0.9 g/L of atrorosin-S.

The molecular weight of sucrose is 324.3 g/mol. When only taking account for the carbon utilisation of the process, the unit c-moles is used. Sucrose has the chemical formula $C_{12}H_{22}O_{11}$, accordingly:

324.3 g/mol correspond to 28.53 g/c-moles $$\left(28.53\ cmoles = \frac{342.3\ g/mol}{12\ carbon\ molecules}\right).$$

20 g of sucrose equal ($n = m/c$-mole = 20 g/28.53 g/cmole) =

$$0.7\ c-mol.$$

The same calculation can be carried out for atrorosin-S and serine

Atrorosin-S: $C_{26}H_{29}NO_9$ and 499.18 g/mol.
Serine: $C_3H_7NO_3$ and 105.09 g/mol.

TABLE 3

Carbon economy atrorosin-S production

| | One-step-fermentation | Two-step-fermentation |
|---|---|---|
| Sucrose (g/L) | 20 | 20 |
| Sucrose (cmole/L) | 0.70 | 0.70 |
| Serine (g/L) | 10 | 1 |
| Serine (cmole/L) | 0.29 | 0.03 |
| Total Carbon in process (cmole) | 0.99 | 0.73 |
| Atrorosin-S (g/L) | 0.9 | 0.9 |
| Atrorosin- S (cmole) | 0.047 | 0.047 |
| Produced atrorosin-s (cmole)/consumed sucrose (cmole) | 0.047/0.99 = 0.048 | 0.047/0.73 = 0.064 |
| Percentage of total Carbon going into atrorosin-S (%) | 4.8% | 6.4% |

The one-step cultivation method converts 4.8% of the carbon into atrorosin-S, while in the corresponding two-step cultivation the conversion of carbon into atrorosin-S was increased to 6.4% (see Table 4). When supplied with $KNO_3$ as nitrogen source, the conversion of carbon into a mixture of pigments was only 1% (Table 4)). Accordingly, the carbon economy of the one-step and two-step fermentation method for the production of an azaphilone pigment attains at least a 4-fold higher yield than traditional fermentation methods based on inorganic nitrogen.

3.6 Enhanced Yields of Pure cis-atrorosin-S are Produced by *T. atroroseus* Using the One- and Two-Step Fermentation Procedure Using traditional fermentation methods based a growth medium comprising inorganic nitrogen (see Table 4), *T. atroroseus* converts carbon into a mixture of pigments with a carbon economy of only 1% or less. In contrast, the carbon economy of the one-step and two-step fermentation method for the production of a single azaphilone pigment with an at least 4-fold higher yield.

Example 4

Products of *T. atroroseus* Produced by the One-Step or Two-Step Fermentation Method are Free of Mycotoxins Analysis of fermentation broth derived from the one-step or two-step fermentation of *T. atroroseus* (supplied with either $KNO_3$, serine, or $KNO_3$ and serine), shows that the mycotoxin citrinin (m/z=251.0920) is not produced (nor mevinolin; not shown) under any of the three cultivation conditions (FIG. 6).

Example 5

Structure of Novel Atrorosin Pigments Produced by Fermentation of *T. atroroseus*

Atrorosin pigments in the fermentation broth of *T. atroroseus* derived from one-step or two-step fermentation were extracted and separated as described in Example 2.1; and subsequently analysed using the following methods:

5.1 Ultra-High Performance Liquid Chromatography-High Resolution Mass Spectrometry (UHPLC-HRMS)

UHPLC-HRMS was performed on an Agilent Infinity 1290 UHPLC system (Agilent Technologies, Santa Clara, Calif., USA) equipped with a diode array detector. Separation was obtained on an Agilent Poroshell 120 phenyl-hexyl column (2.1×250 mm, 2.7 μm) with a linear gradient consisting of water (A) and acetonitrile (B) both buffered with 20 mM formic acid, starting at 10% B and increased to 100% in 15 min where it was held for 2 min, returned to 10% in 0.1 min and remaining for 3 min (0.35 mL/min, 60° C.). An injection volume of 1 μL was used. MS detection was performed in positive detection mode on an Agilent 6545 QTOF MS equipped with Agilent Dual Jet Stream electrospray ion source with a drying gas temperature of 250° C., gas flow of 8 L/min, sheath gas temperature of 300° C. and flow of 12 L/min. Capillary voltage was set to 4000 V and nozzle voltage to 500 V. Mass spectra were recorded at 10, 20 and 40 eV as centroid data for m/z 85-1700 in MS mode and m/z 30-1700 in MS/MS mode, with an acquisition rate of 10 spectra/s. Lock mass solution in 70:30 methanol:water was infused in the second sprayer using an extra LC pump at a flow of 15 μL/min using a 1:100 splitter. The solution contained 1 μM tributylamine (Sigma-Aldrich) and 10 μM Hexakis(2,2,3,3-tetrafluoropropoxy)phosphazene (Apollo Scientific Ltd., Cheshire, UK) as lock masses. The $[M+H]^+$ ions (m/z 186.2216 and 922.0098 respectively) of both compounds was used.

TABLE 4

Effect of fermentation conditions on pigment profile and yield

| Nitrogen Source | 0.1M $KNO_3$ | 0.1M $NH_4NO_3$ | 0.1M $(NH_4)_2SO_4$ | One-step cultivation Serine | Two-step cultivation Serine |
|---|---|---|---|---|---|
| Carbon conversion to pigment* | 1.2% Pigment mixture | 0.5% Pigment mixture | 0.8% Pigment mixture | 4.8% Atrororosin-S | 6.4% Atrororosin-S |

* Each fermentation was performed at 30° C. at a pH of 4.5.

5.2 Nuclear Magnetic Resonance (NMR) Spectroscopy 1D and 2D NMR spectra (1 H, DQF-COSY, edHSQC, HMBC and NOESY) were recorded on either a Bruker Ascend 400 MHz (Bruker, Billerica, Mass., USA), or on a Bruker Avance 800 MHz located at the Department of Chemistry at the Technical University of Denmark. NMR spectra were acquired using standard pulse sequences. The solvent used was either DMSO-d6, which was also used as reference with signals at $\delta H=2.50$ ppm and $\delta C=39.5$ ppm, or $CD_3OD$ (reference at $\delta H=3.31$ ppm and $\delta C=49.0$ ppm). Data processing and analysis was done using TopSpin 3.5 (Bruker), MestReNova v.6.2.1-7569 (Mestrelab Research, Santiago de Compostela, Spain) and ACD NMR Workbook (Advanced Chemical Development, Inc., Toronto, Ontario, Canada). J-couplings are reported in hertz (Hz) and chemical shifts in ppm ($\delta$).

5.3 Structural Elucidation of cis-atrorosin-S

The purified atrorosin-S was a dark red, almost black, amorphous solid. HR-ESI-MS gave a mass-to-charge ratio of $[M+H]^+=500.1915$ Da, corresponding to a molecular formula of $C_{26}H_{30}NO_9$ (DBE=13).

TABLE 5

Proton and carbon shifts, and coupling constants for atrorosin-S.

| # | 1H | 13C | mult. |
|---|---|---|---|
| 1-OH | — | — | — |
| 1 | — | 166.8 | — |
| 2 | 6.43 | 130.9 | d (J = 11.8) |
| 3 | 6.94 | 133.8 | d (J = 11.8) |
| 4 | — | 149.7 | — |
| 5 | 6.81 | 119.6 | S |
| 6 | — | 151.8 | — |
| 7 | 6.72 | 117.7 | S |
| 8 | — | 168.0 | — |
| 9 | — | 86.8 | — |
| 9-CH3 | 1.67 | 30.1 | S |
| 10 | — | 195.4 | — |
| 11 | — | 98.6 | — |
| 12 | 8.57 | 142.8 | S |
| 13 | — | 174.6 | — |
| 14 | — | 125.4 | — |
| 15 | — | 198.5 | — |
| 16 | 2.82 | 40.9 | M |
| 17 | 1.59 | 25.8 | quint (J = 7.0 Hz) |
| 18 | 1.31 | 23.3/30.0/32.5 | |
| 19 | 1.31 | 23.3/30.0/32.5 | M |
| 20 | 1.31 | 23.3/30.0/32.5 | |
| 21 | 1.31 | 23.3/30.0/32.5 | |
| 22 | 0.89 | 13.9 | t (J = 7.3) |
| 1'-OH | — | — | — |
| 1' | — | 169.1 | — |
| 2' | 5.12 | 67.3 | dd (J = 5.4/2.9) |
| 3'a | 4.28 | 62.5 | dd (J = 12.2/5.4) |
| 3'b | 4.09 | 62.5 | dd (J = 12.2/2.9) |

Cis-atrorosin-S had a UV absorption spectrum similar to that of known monascorubramines, with $UV_{max}$ at 520 nm. 1D and 2D NMR (shifts listed in Table 5) were used to determine its structure.

$^1$H-NMR and HSQC revealed five olefinic protons in the range from 6.43 to 8.57 ppm (2, 3, 5, 7, and 12), and two methyl groups at 1.67 (9-CH3) and 0.89 ppm (22). In addition, a total of seven CH2 groups could be identified, six of these linked together in a fatty acid chain (16-21), and one (3') linked to a CH at 5.12 ppm (2').

$^{13}$C-NMR and HMBC revealed 11 quaternary carbons: Five carbonyls (1, 10, 13, 15, and 1'), five alkene carbons (4, 6, 8, 11, and 14), and one quaternary alkane (9).

HMBC provided long-range H—C-couplings within the azaphilone scaffold, linking 3' to the carbonyl 1'. 3' also showed coupling to 4. 16 and 17 had correlations to 15, and 5 and 12 had correlations to 6, 10 and 10, while 7 and 9-$CH_3$ showed couplings to 8 and 9. In addition, couplings to 1 and 4 from 2 and 3 were observed. Finally coupling constants between 2 and 3 supported cis configuration of the double bond. Based on the obtained spectra, atrorosin-S was determined to have the structure set out in FIG. 7.

5.4 Structural Elucidation of Atrorosin-Amino Acid Derivatives

The structure of the remaining 18 atrorosin-amino acid derivatives was elucidated to confirm that the respective amino acid was incorporated into the core azaphilone structure as for cis-atrorosin-S (data not shown). The NMR data only showed differences from cis-atrorosin-S in the amino acid moiety attached to the isoquinoline part of the molecule. All of the 18 atrorosin-amino acid derivatives had a bright red color.

Example 6

Physical Properties of Atrorosin Pigments

6.1 Hydrophilicity of Atrorosin Pigments in Comparison to Respective Monascorubramine (Without Carboxylic Acid in Position 1 as in All Atrorosins)

The logP and logD values are a measure of the solubility of an analyte in a two-phase water/octanol system. The lower the value the more hydrophilic the analyte, with a logP/D value of 0 corresponding to a 50:50 distribution. logP refers to only unionized species, whereas the logD refers to both ionized and unionized species and therefore varies with pH.

TABLE 5

LogP values for atrorosin and monascorubramine pigments

| Name | LogP ± uncertainty |
|---|---|
| Atrorosin-A | 0.81 ± 0.67 |
| Monascorubramine A | 2.43 ± 0.65 |
| Atrorosin-C | 1.72 ± 0.72 |
| Monascorubramine C | 3.38 ± 0.7 |
| Atrorosin-D | 0.82 ± 0.71 |
| Monascorubramine D | 2.48 ± 0.68 |
| Atrorosin-E | 0.05 ± 0.69 |
| Monascorubramine E | 1.68 ± 0.66 |
| Atrorosin-F | 2.67 ± 0.68 |
| Monascorubramine F | 4.31 ± 0.65 |
| Atrorosin-G | 0.46 ± 0.67 |
| Monascorubramine G | 2.09 ± 0.65 |
| Atrorosin-H | 0.29 ± 0.71 |
| Monascorubramine H | 1.93 ± 0.58 |
| Atrorosin-I | 2.22 ± 0.68 |
| Monascorubramine I | 3.84 ± 0.65 |
| Atrorosin-K | 0.45 ± 0.68 |
| Monascorubramine K | 2.08 ± 0.65 |
| Atrorosin-L | 2.22 ± 0.668 |
| Monascorubramine-L | 3.84 ± 0.65 |
| Atrorosin-M | 1.86 ± 0.74 |
| Monascorubramine M | 3.48 ± 0.71 |
| Atrorosin-N | −0.02 ± 0.72 |
| Monascorubramine N | 1.64 ± 0.7 |

TABLE 5-continued

LogP values for atrorosin and monascorubramine pigments

| Name | LogP ± uncertainty |
|---|---|
| Atrorosin-Q | −0.19 ± 0.77 |
| Monascorubramine Q | 1.44 ± 0.75 |
| Atrorosin-R | −0.3 ± 0.73 |
| Monascorubramine R | 1.32 ± 0.72 |
| Atrorosin-S | −0.38 ± 0.72 |
| Monascorubramine S | 1.29 ± 0.69 |
| Atrorosin-T | −0.03 ± 0.72 |
| Monascorubramine T | 1.63 ± 0.7 |
| Atrorosin-V | 1.68 ± 0.68 |
| Monascorubramine V | 3.31 ± 0.65 |
| Atrorosin-W | 2.59 ± 0.69 |
| Monascorubramine W | 4.23 ± 0.66 |
| Atrorosin-Y | 1.39 ± 0.69 |
| Monascorubramine Y | 3.57 ± 0.66 |

The LogP and logD values, are presented for atrorosin-S and atrorosin-E in FIG. 8, demonstrate that they are more soluble.

6.2 Colorimetric Values of Atrorosin Pigments

Color characteristics of the atrorosin pigments were determined using CIELAB color system (15). The values of L*, a*, and b* were measured by a CR-300 colorimeter with the CIELAB color system (Minolta Camera Co., Ltd., Osaka, Japan). These values were then used to calculate chroma (C*) and hue angle (hab) values. L* indicates lightness from 0 (black) to 100 (white). Positives and negatives in a* represent red and green, respectively, whereas positives and negatives in b* represent yellow and blue, respectively. Chroma values denote the saturation or purity of the color. Values close to the center at the same L* value indicate dull or gray colors, whereas values near the circumference represent vivid or bright colors. Hue angle values represent 0 for redness, 90 for yellowness, 180 for greenness, and 270 for blueness. L*, a*, and b* values of the pure pigments were obtained after their dilution concentration was adjusted to 4.

The invention claimed is:

1. A method for producing an atrorosin pigment by fermentation, comprising the steps of:
   a) providing spores or mycelia of a species of the genus *Talaromyces*,
   b) cultivating the spores or mycelia of (a) in a liquid growth medium comprising a sole nitrogen source,
   c) recovering the atrorosin pigment produced during said cultivating in step b), and
   d) optionally isolating said atrorosin pigment,
   wherein the pH of the growth medium in step (b) is maintained between 4 and 6;
   wherein the sole nitrogen source in said liquid growth medium in step (b) is one compound selected from the group consisting of a single amino acid, a peptide, an amino sugar and a primary amine; and
   wherein the atrorosin pigment has the structure of Formula I

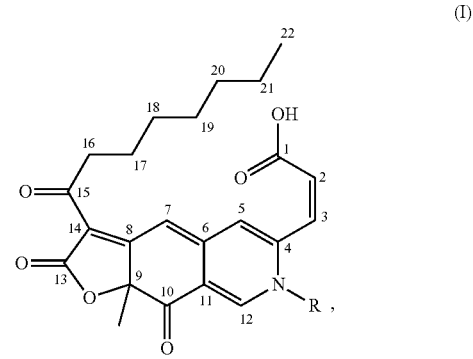

wherein N-R is selected from the group consisting of an amino acid, a peptide, an amino sugar and a primary amine, and the configuration of the double bond between carbon 2 and 3 is cis.

2. The method for producing an atrorosin pigment by fermentation according to claim 1, comprising the additional step of:
   a') cultivating the spores or mycelia of (a) in a preliminary liquid growth medium, comprising a sole nitrogen source,
      wherein the sole nitrogen source in the preliminary liquid growth medium is an inorganic nitrogen source and the concentration of $NO_3^-$ is no more than 20 mM, continuing cultivation till the concentration of $NO_3^-$ is depleted to less than 5 mM; and
   wherein said step (a') is followed by step (b).

3. The method according to claim 2, wherein the sole nitrogen source in step (a') is an inorganic nitrogen source selected from the group consisting of $KNO_3$ and $NaNO_3$.

4. The method according to claim 1, wherein the sole nitrogen source in step (b) is a single amino acid, selected from the group consisting of: L-alanine, L-arginine, L-asparagine, L-aspartate, L-cysteine, L-glutamine, L-glutamate, L-glycine, L-histidine, L-isoleucine, L-leucine, L-lysine, L-methionine, L-phenylalanine, L-serine, L-threonine, L-tyrosine, L-valine and L-ornithine.

5. The method according to claim 1, wherein the species is *Talaromyces atroroseus*.

6. The method according to claim 2, wherein the preliminary liquid growth is synthetic, and comprises salts, trace metals and a carbon source, wherein the salts are $KH_2PO_4$, NaCl, $MgSO_4 \cdot 7H_2O$, KCl, and $CaCl_2 \cdot H_2O$ and the trace metals are $CuSO_4 \cdot 5H_2O$, $Na_2B_4O_7 \cdot 10H_2O$, $FeSO_4 \cdot 7H_2O$, $MnSO_4 \cdot H_2O$, $NA_2MoO_4 \cdot 2H_2O$, and $ZnSO_4 \cdot 7H_2O$.

7. The method according to claim 6, wherein the carbon source is selected from among glucose, sucrose, maltose, soluble starch, beet or cane molasses, malt, and any combination of at least two thereof.

8. The method according to claim 1, wherein fermentation is performed using batch or fed batch fermentation under aerobic conditions.

9. The method according to claim 1, wherein the liquid growth medium in step (b) is maintained within a pH of 4.0 to 5.5.

10. An atrorosin pigment having the structure of Formula I,

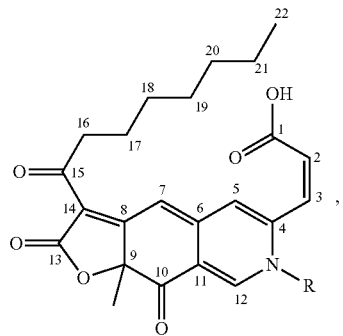

(I)

wherein N-R is selected from among an amino acid, a peptide, an amino sugar and a primary amine, and the configuration of the double bond between carbon 2 and 3 is cis, and wherein the amino acid is selected from the group consisting of: L-alanine, L-arginine, L-asparagine, L-aspartate, L-cysteine, L-glutamate, L-glycine, L-histidine, L-isoleucine, L-leucine, L-lysine, L-methionine, L-phenylalanine, L-serine, L-threonine, L-tyrosine, L-valine and L-ornithine.

11. A product comprising the atrorosin pigment according to claim 10, wherein the product is selected from among a food, a non-food product and a cosmetic.

12. A kit for coloring a product, wherein the kit comprises at least one atrorosin pigment according to claim 10, wherein the pigment is supplied in a container, wherein the product is selected from among a food, a non-food product and a cosmetic.

13. A colouring agent for any one of a food, a non-food product and a cosmetic, comprising the atrorosin pigment according to claim 10.

14. The method according to claim 1, wherein the liquid growth medium is synthetic, and comprises salts, trace metals and a carbon source, wherein the salts are $KH_2PO_4$, NaCl, $MgSO_4 \cdot 7H_2O$, KCl, and $CaCl_2 \cdot H_2O$ and the trace metals are $CuSO_4 \cdot 5H_2O$, $Na_2B_4O_7 \cdot 10H_2O$, $FeSO_4 \cdot 7H_2O$, $MnSO_4 \cdot H_2O$, $NA_2MoO_4 \cdot 2H_2O$, and $ZnSO_4 \cdot 7H_2O$.

* * * * *